United States Patent
Xu et al.

(10) Patent No.: US 12,274,709 B2
(45) Date of Patent: Apr. 15, 2025

(54) DUAL-DRUG CO-DELIVERY SYSTEM, PREPARATION METHOD THEREFOR AND USE THEREOF

(71) Applicant: Institute of Basic Medical Sciences Chinese Academy of Medical Sciences, Beijing (CN)

(72) Inventors: Haiyan Xu, Beijing (CN); Doudou Yan, Beijing (CN); Jie Meng, Beijing (CN); Jian Liu, Beijing (CN); Tao Wen, Beijing (CN); Yangyang Ge, Beijing (CN)

(73) Assignee: INSTITUTE OF BASIC MEDICAL SCIENCES CHINESE ACADEMY OF MEDICAL SCIENCES, Beijing (CN)

( * ) Notice: Subject to any disclaimer, the term of this patent is extended or adjusted under 35 U.S.C. 154(b) by 778 days.

(21) Appl. No.: 17/433,716

(22) PCT Filed: Feb. 27, 2020

(86) PCT No.: PCT/CN2020/076891
§ 371 (c)(1),
(2) Date: Aug. 25, 2021

(87) PCT Pub. No.: WO2020/173475
PCT Pub. Date: Sep. 3, 2020

(65) Prior Publication Data
US 2022/0047613 A1    Feb. 17, 2022

(30) Foreign Application Priority Data
Feb. 27, 2019   (CN) .......................... 201910146784.1

(51) Int. Cl.
| | | |
|---|---|---|
| *A61K 31/704* | (2006.01) | |
| *A61K 9/08* | (2006.01) | |
| *A61K 9/107* | (2006.01) | |
| *A61K 31/55* | (2006.01) | |
| *A61K 47/10* | (2017.01) | |
| *A61K 47/34* | (2017.01) | |
| *A61P 35/02* | (2006.01) | |

(52) U.S. Cl.
CPC .............. *A61K 31/704* (2013.01); *A61K 9/08* (2013.01); *A61K 9/1075* (2013.01); *A61K 31/55* (2013.01); *A61K 47/10* (2013.01); *A61K 47/34* (2013.01); *A61P 35/02* (2018.01)

(58) Field of Classification Search
CPC ...... A61K 47/32; A61K 47/34; A61K 9/1075; A61K 31/704
See application file for complete search history.

(56) References Cited

FOREIGN PATENT DOCUMENTS

| | | |
|---|---|---|
| CN | 105055375 A | 11/2015 |
| CN | 109745288 A | 5/2019 |

OTHER PUBLICATIONS

Shim (Pharm Res, 2014, 31:2178-2185).*
International Preliminary Report on Patentability dated Sep. 2, 2021 received in International Application No. PCT/CN2020/076891.
International Search Report dated May 27, 2020 issued in PCT/CN2020/076891.
Shim, G. et al., "Liposomal Co-Delivery of Omacetaxine Mepesuccinate and Doxorubicin for Synergistic Potentiation of Antitumor Activity", Pharmaceutical Research (2014), vol. 31, No. 8, pp. 2178-2185.
Non-official translation: Beijing No. 8 High School Youth Academy of Sciences. 2018 Thesis Proposal Presentation by NAN. Ziyi: Preparation of Nanomicelle-based Dual-Drug Delivery and Anti-leukemia Effect), https://v.youku.comlv_show/id_ XMzcxNDg3NTA2MA==. html, Jul. 10, 2018 (Jul. 10, 2018), with English translation of the title and contents of the presentation.
Xiang, Jin et al., "Soluplus® micelles as a potential drug delivery system for reversal of resistant tumor," Biomedicine & Pharmacotherapy (Dec. 24, 2014), pp. 1-8.
Edited by Yuan, Yingjin, Non-official translation: Method for Preparing Micelles and Formation Mechanism thereof, (Non-official translation: Current Pharmaceutical Technology (Jan. 31, 2006), vol. 2), with English summary of the last three paragraphs on p. 152.
Yang, Liu, "The Effects of Homoharringtonine and Adriamycin Combination Treatment on the Leukemia Cells", Medicine & Public Health, China Master's Theses Full-Text Database (Mar. 15, 2017), with English Abstract; cited asa Category "Y" reference in the International Search Report as relevant to claims 1-15.

* cited by examiner

*Primary Examiner* — Pancham Bakshi
(74) *Attorney, Agent, or Firm* — Scully, Scott, Murphy & Presser, P.C.

(57) ABSTRACT

The present invention discloses a dual-drug co-delivery system, a preparation method therefor and use thereof, the dual-drug co-delivery system being prepared from raw materials comprising a block copolymer, Homoharringtonine and Doxorubicin hydrochloride. The dual-drug co-delivery system provided by the present invention has a stronger killing effect on various hematologic tumors and solid tumor cells, can provide a feasible drug delivery system for inhibiting tumor growth and leukemia treatment, and has broad prospects.

16 Claims, 4 Drawing Sheets

DUAL-DRUG CO-DELIVERY SYSTEM, PREPARATION METHOD THEREFOR AND USE THEREOF

FIELD OF THE INVENTION

The present invention relates to the field of pharmaceutical technology and in particular to a dual-drug co-delivery system, a preparation method therefor and its use in the preparation of antitumor drugs.

BACKGROUND OF THE INVENTION

Chemotherapy is a treatment that uses chemical drugs to stop the proliferation, infiltration and metastasis of cancer cells until they are finally killed, and is the main treatment for most solid tumors and hematologic tumors. The chemical drugs used in the chemotherapy process are called chemotherapeutic drugs. Due to the emergence of chemotherapy drug resistance and dose-dependent toxic side effects, a single drug can no longer meet clinical needs, so the combination of multiple chemotherapeutic drugs is used to solve this problem. Although the combined use of multiple chemotherapeutic drugs may reduce the possibility of drug resistance caused by a single drug, there are problems with the high number of doses administered and the dose distribution regimes being not easily determined.

A chemotherapeutic drug co-delivery system is an effective method to solve the above problems. The co-delivery system encapsulates two or more chemotherapeutic drugs in a carrier and utilizes the synergistic effect between the drugs to enhance its killing effect on tumor cells. Compared with single drug and drugs used in combination, the advantages of drug co-delivery system are: 1) two or more chemotherapeutic drugs exert a synergistic effect to produce a stronger anti-tumor effect at a smaller dose, reduce toxic side effects, and avoid the generation of drug resistance; 2) the time and space of drug release can be controlled to coordinate the pharmacokinetics and pharmacodynamics of different drugs; 3) reducing the number of administrations and improve patient compliance; 4) single dosage of administration to avoid the uncertainty of dose distribution when multiple drugs are administered.

Drug co-delivery systems mainly use liposomes, polymer micelles, solid lipid nanoparticles, and inorganic nanomaterials such as mesoporous silicon nanoparticles, gold nanoparticles, magnetic nanoparticles, carbon nanotubes and so on as drug co-delivery carriers. There may be many types of drugs delivered. For example, two small-molecule chemotherapeutic drugs acting on different targets are delivered to achieve the maximum anti-tumor effect and reduce the possibility of generating drug resistance. Another example is the co-delivery of chemotherapeutic drugs and siRNA, which uses RNA interference technology to silence drug-resistant genes and interferes with cellular signaling pathways to overcome drug resistance. Another example is the co-delivery of chemotherapeutic drugs and imaging agents to achieve targeted drug delivery and non-invasive tumor imaging.

Most of the existing studies on drug co-delivery systems focus on chemotherapy treatment of solid tumors, including breast cancer, liver cancer, cervical cancer, prostate cancer, lung cancer, brain tumors, head and neck squamous cell carcinoma, pancreatic cancer, gastric cancer, melanoma, and ovarian cancer. Because of the large number of hematologic tumor types and the complexity of subtypes within each type impose many limitations on the types of drugs available to treat them, making the number of drugs available to treat hematologic tumors less than those available to treat solid tumors, there are few drug co-delivery systems applicable to hematologic tumors such as leukemia, lymphoma, and myelodysplastic syndromes to date, and greater challenges are faced in chemotherapy. Except for a small amount of basic research, the only drugs currently available for the preparation of drug co-delivery systems for the treatment of hematologic tumors are Cytarabine and Daunorubicin. The drug co-delivery system formed from them is the liposomal co-delivery system (CPX-351), which entered phase III clinical trials in November 2014. Experiments have shown CPX-351 to be effective in elderly patients with primary or relapsed acute myeloid leukemia (AML), which can be taken as remission induction therapy for patients who have failed standard induction therapy or as consolidation therapy for patients who have received a stem cell transplant or who have not undergone a stem cell transplant. However, the preparation process of the above liposomal co-delivery system is complex, and requires not only the use of multiple lipid materials, but also the preparation in a copper gluconate/triethylamine buffer system to allow the formation of complexes of the drugs Cytarabine and Daunorubicin with copper ions in the buffer system (containing organic solvents) in a certain molar ratio, thus ensuring the retention time of the drugs in the liposomes. The liposomal co-delivery system involves the use of organic solvents, and therefore has the problem of high risk of toxic side effects.

Therefore, there is an urgent need in this field to develop a new drug co-delivery system suitable for hematologic tumors, especially relapsed and refractory leukemia.

SUMMARY OF THE INVENTION

The purpose of the present invention is to provide, in the first aspect, a dual-drug co-delivery system with strong antitumor effects, low toxic side effects, and for refractory leukemia, directed to the technical defects existing in the prior art. The dual-drug co-delivery system is prepared from raw materials including a block copolymer, Homoharringtonine and Doxorubicin hydrochloride. The block copolymer is selected from one or more of polyethylene caprolactam-polyvinyl acetate-polyethylene glycol (Soluplus), methoxy polyethylene glycol-polycaprolactone (mPEG-PCL), distearoyl phosphatidylethanolamine-polyethylene glycol 2000 (DSPE-PEG$_{2000}$), polyoxyethylene polyoxypropylene ether block copolymer, polylactic acid-hydroxyacetic acid copolymer (PLGA), preferably Soluplus.

The ratio of Homoharringtonine, Doxorubicin hydrochloride, and block copolymer in parts by weight is (1-10):(1-40):(4-200); preferably (1-5):(3-15):(45-200).

The average hydration diameter of the dual-drug co-delivery system is 20-200 nm, preferably 60-180 nm.

The molecular weight ratio of polyethylene caprolactam, polyvinyl acetate and polyethylene glycol in the block copolymer Soluplus is 57:30:13.

The ratio of Homoharringtonine, Doxorubicin hydrochloride, and block copolymer Soluplus in parts by weight is (1-10):(1-40):(4-200); preferably (1-5):(3-15):(45-200).

In the second aspect, the present invention provides a method for preparing the above-mentioned dual-drug co-delivery system, which comprises preparing micelle loaded with Homoharringtonine and loading Doxorubicin.

Preferably, the micelle loaded with Homoharringtonine is obtained by mixing and stirring Homoharringtonine, block copolymer and phosphate buffer. The specific preparation process includes the following steps of:

1) Adding the block copolymer and Homoharringtonine to the phosphate buffer, heating and stirring to obtain a liquid B;
2) Filtering the liquid B obtained in step 1), and the filtrate is the micelles loaded with Homoharringtonine, called micelle C.

The step of loading Doxorubicin is to mix the micelle loaded with Homoharringtonine and a phosphate buffer containing a block copolymer, and then add an aqueous solution of Doxorubicin hydrochloride and stir. It specifically includes the following steps of:
(1) Dissolving the block copolymer in the phosphate buffer to obtain a clear solution D;
(2) Mixing the clear solution D obtained in step (1) with the micelle loaded with Homoharringtonine (micelle C), and adding the aqueous solution of Doxorubicin hydrochloride dropwise under heating and stirring (preferably, the concentration of Doxorubicin hydrochloride in the aqueous solution of Doxorubicin hydrochloride is 3-8 mg/mL) to obtain a liquid E;
(3) Filtering the liquid E obtained in step (2), and the filtrate is the dual drug co-delivery system.

The heating is heated to 25-70° C.

The stirring speed is 100-1000 r/min.

In the third aspect, the present invention provides the use of the above-mentioned dual-drug co-delivery system in the preparation of drugs for the inhibition of tumor growth-related diseases or for the treatment of leukemia.

The tumor growth-related diseases are tumors for which the combination of Homoharringtonine and anthracycline antibiotics are effective, including but not limited to acute myeloid leukemia, chronic myeloid leukemia, cervical cancer and the like.

The acute myeloid leukemia is a refractory AML1-ETO acute myeloid leukemia.

The acute myeloid leukemia is AML1-ETO acute myeloid leukemia characterized by a t (8; 21)(q22; q22) chromosomal translocation, commonly seen in M2 in FAB typing, where the AML1 gene on chromosome 21 q22 and the ETO gene on chromosome 8 q22 rearrange to form an AML1-ETO fusion gene.

The block copolymer used as carrier in the dual-drug co-delivery system provided by the present invention is amphiphilic high-molecular polymer that forms a hydrophilic shell-hydrophobic core structure in aqueous solutions. The amphiphilic block copolymer forms micelles in the phosphate buffer solution, and two drugs, Homoharringtonine (hydrophobic) and Doxorubicin hydrochloride (hydrophilic), are assembled into the hydrophobic cores of the micelle successively by a two-step assembly method, forming a dual-drug co-delivery system that can realize combined administration. The dual-drug co-delivery system of the present invention can also exert different therapeutic effects on tumors by adjusting the ratio of the two drugs in the micelle. The dual-drug co-delivery system of the present invention has a stronger killing effect on a variety of hematologic tumors and solid tumor cells. Tumor cells include acute myeloid leukemia cells, chronic myeloid leukemia cells, cervical cancer cells, and breast cancer cells. The system can also be used as a medicine for the treatment of refractory AML1-ETO acute myeloid leukemia with excellent effects. In particular, in the leukemia cell experiment, compared with the combined use of Doxorubicin and Homoharringtonine, the dual-drug co-delivery system of the present invention can more effectively inhibit the proliferation of myeloid leukemia cells. In animal experiments, it has a better therapeutic effect on AML1-ETO mice with acute myeloid leukemia, which can prolong the survival period of mice while reducing toxic side effects. The dual-drug co-delivery system of the present invention can be used in the inhibition of tumor growth and in the treatment of leukemia.

The dual-drug co-delivery system of the present invention does not use any organic solvent in the preparation process, has high safety, and meets the requirements of clinical medication; and the preparation process is simple and suitable for industrial production.

DETAILED DESCRIPTION OF THE INVENTION

Figure 1:
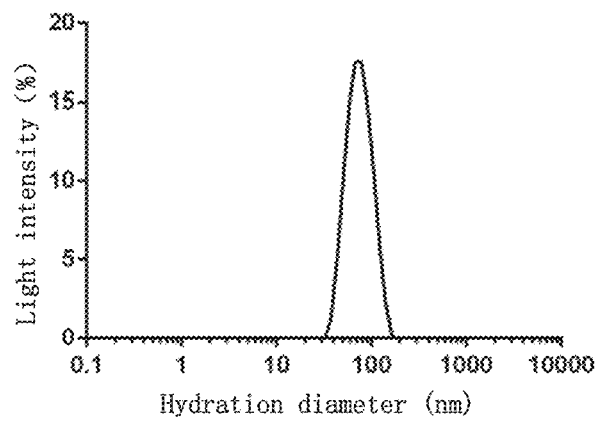
FIG. 1 is a graph of the particle size distribution of the dual-drug co-delivery system of the present invention in the phosphate buffer.

Homoharringtonine (HHT) is a biologically active ingredient extracted from plants of *Cephalotaxus* genus, which can inhibit the proliferation of leukemia cells and induce cell apoptosis. Doxorubicin hydrochloride is a broad-spectrum anti-tumor drug that exhibits anti-tumor effects by destroying DNA structure. Homoharringtonine and Doxorubicin (DOX) hydrochloride are hydrophobic and hydrophilic drugs, respectively, and can be used clinically in the combined treatment of acute myeloid leukemia. However, separated administration of the two drugs in the treatment of acute myeloid leukemia can lead to poor patient compliance. In addition, due to different pharmacokinetics, the concentrations of the two drugs in the body cannot maintain the set ratio.

In terms of co-delivery systems for these two drugs, there is only one literature report on liposome co-delivery systems (Shim G, Lee S, Choi J, et al. Liposomal Co-Delivery of Omacetaxine Mepesuccinate and Doxorubicin for Synergistic Potentiation of Antitumor Activity. Pharmaceutical Research, 2014, 31(8):2178-2185.), wherein the delivery system uses liposomes as a carrier, with a particle size of 126 nm, which has an effect of inhibiting tumor growth in a model of subcutaneous transplantation of cervical cancer cells (HeLa cells) in mice. The preparation process of the liposome co-delivery system is complicated and requires using a variety of lipid materials and adding organic solvent methanol to enable Homoharringtonine to be firstly encapsulated in liposomes and then to further encapsulate Doxorubicin hydrochloride by electrostatic interaction. The presence of the organic solvent methanol in the liposome co-delivery system will bring toxic side effects. In addition, the liposome co-delivery system is designed to inhibit the growth of solid tumor HeLa cells. Liposomes are relatively stable, and usually use the high permeability and retention effect of solid tumors to accumulate and release drugs in tumor tissues, but cannot effectively kill leukemia cells in the circulating blood. Moreover, if the liposome co-delivery system accumulates in the bone marrow, it is difficult to reduce the inhibitory effect of the drug itself on the growth of bone marrow cells, and the treatment of acute myeloid leukemia requires the participation of bone marrow cells, therefore, the liposome co-delivery system disease is not suitable for use in the treatment of acute myeloid leukemia.

Polymeric micelles are a class of co-delivery drug carriers that have received widespread attention. Because its general size is tens of nanometers, it is also called nanomicelle. It is spontaneously formed by an amphiphilic polymer in a solvent system at a suitable concentration and temperature, and encapsulates the drugs in the hydrophobic core of the micelle through the hydrophilic-hydrophobic interaction, thus it is usually used as a co-delivery drug carrier for two hydrophobic drugs. Its advantage is that it does not affect the activity of the drug itself and significantly solubilizes the hydrophobic drug, and the preparation method is simple and does not require using organic solvents. However, conventionally designed polymeric micelles are difficult to apply to hydrophilic drugs; especially it is difficult to load both hydrophobic and hydrophilic drugs into the hydrophobic core of the micelles at the same time.

Since Doxorubicin hydrochloride is water-soluble, while Homoharringtonine is hydrophobic, according to general understanding, it is difficult to use polymeric micelles as the co-delivery drug carrier of the above-mentioned dual drugs, and to encapsulate two drugs with different hydrophilic and hydrophobic properties into the hydrophobic core of the micelle. By using the selected unique polymer as a carrier, the present invention encapsulates two drugs with different hydrophilic and hydrophobic properties into one polymeric micelle without using any organic solvents, and uses the polymer micelle to form a co-delivery system.

The dual-drug co-delivery system of the present invention uses amphiphilic block copolymer as carrier, which can form micelle with a hydrophilic shell-hydrophobic core structure in an aqueous solution. Through the hydrophobic effect, the Homoharringtonine is first encapsulated in the hydrophobic core of the micelle, and then Doxorubicin hydrochloride is assembled into the hydrophobic core of the micelle to form the dual-drug co-delivery system of the present invention. That is, the amphiphilic block copolymer is used to co-deliver Doxorubicin hydrochloride and Homoharringtonine.

The block copolymer used in the dual-drug co-delivery system of the present invention is selected from one or more of polyethylene caprolactam-polyvinyl acetate-polyethylene glycol (for example, a product under the trade name of Soluplus), methoxy polyethylene glycol-polycaprolactone (mPEG-PCL), distearoyl phosphatidylethanolamine-polyethylene glycol 2000 (DSPE-PEG$_{2000}$), polyoxyethylene polyoxypropylene ether block copolymer, polylactic acid-hydroxyacetic acid copolymer (PLGA), preferably Soluplus. Available block copolymers are commercially available, with an average molecular weight of 1,000-150,000.

The invention also provides the use of the dual-drug co-delivery system formed by Doxorubicin hydrochloride and Homoharringtonine in the preparation of anti-tumor drugs.

The dual-drug co-delivery system of the present invention is particularly useful as a drug for the treatment of refractory acute myeloid leukemia, including AML1-ETO acute myeloid leukemia, which is characterized by t (8;21) (q22; q22) chromosomal translocation, which is common in M2 in FAB typing and is present in approximately 12% to 15% of AML patients; where the AML1 gene on chromosome 21 q22 and the ETO gene on chromosome 8 q22 are rearranged to form the AML1-ETO fusion gene.

The following describes the content of the present invention in more detail with reference to specific examples, and further explains the present invention, but these examples do not limit the present invention by any means.

Unless otherwise specified, cell lines used in the following examples are all purchased from the National Infrastructure of Cell line Resource.

Unless otherwise specified, the phosphate buffers used in the following examples are all 1×PBS solutions (pH 7.4); the solvents of the aqueous solutions used are all ultrapure water.

Example 1: Preparation of Micelles Loaded with Homoharringtonine (1) 15.0-100.0 mg of block copolymer and 5.0 mg of Homoharringtonine were dissolved in 4 mL of phosphate buffer, and stirred to obtain polymer suspension A; the block copolymer is selected from one or more of polyethylene caprolactam-polyvinyl acetate-polyethylene glycol (Soluplus), methoxy polyethylene glycol (mPEG)-polycaprolactone (PCL) (mPEG-PCL, molecular weight: 4000 D), distearoyl phosphatidylethanolamine (DSPE)-polyethylene glycol 2000 (PEG$_{2000}$) (DSPE-PEG$_{2000}$, molecular weight: 2807 D), polyoxyethylene polyoxypropylene ether block copolymer (purchased from BASF, Germany, molecular weight 9840 D-14600 D, the content ratio of polyoxyethylene and polyoxypropylene is 80:20), polylactic acid-hydroxyacetic acid copolymer (PLGA, 10 KD-40 KD, the content ratio of polylactic acid and glycolic acid is 50:50), preferably Soluplus (commercially available from BASF, Germany, molecular weight 120 KD, the molecular weight ratio of polyethylene caprolactam, polyvinyl acetate and polyethylene glycol is 57:30:13);

(2) The polymer suspension A was heated at 25-70° C. and stirred at 100-1000 r/min for 20-120 min to obtain a solution B;

(3) The solution B was allowed to stand at room temperature for about 1 hour until it was clear and transparent, and then was filtered with a 0.22 μm polyethersulfone water-based filter membrane to remove the free drug that was not encapsulated into the micelle to obtain micelle C loaded with Homoharringtonine; the average hydration diameter of the obtained micelle C loaded with Homoharringtonine was 70 nm, the drug loading was 14%, and the encapsulation efficiency was 64%.

According to the above method, a series of micelles C loaded with Homoharringtonine were prepared. Only the raw material compositions and preparation parameters used were adjusted. See Table 1 for details.

TABLE 1

Preparation parameters of micelle C loaded with Homoharringtonine

| Micelle C loaded with homoharringtonine | Block copolymer | | Homohaningtonine | Heating temperature/ °C. | Stirring Rotate speed/r/min | Stirring time/min | Average hydration diameter/ nm | Drug loading/ % | Encapsulation efficiency/ % |
|---|---|---|---|---|---|---|---|---|---|
| C-1 | Soluplus | 15 mg | 5 mg | 50 | 500 | 60 | 70 | 14 | 64 |
| C-2 | mPEG$_{2000}$-PCL$_{20000}$ | 15 mg | 5 mg | 60 | 300 | 120 | 80 | 16 | 58 |
| C-3 | DSPE-PEG$_{2000}$ | 50 mg | 5 mg | 30 | 800 | 100 | 55 | 6 | 60 |
| C-4 | PLGA | 50 mg | 5 mg | 25 | 100 | 80 | 150 | 5 | 50 |
| C-5 | polyoxyethylene polyoxypropylene ether block copolymer | 75 mg | 5 mg | 40 | 1000 | 20 | 120 | 3 | 40 |
| C-6 | mPEG$_{2000}$-PCL$_{20000}$ + PLGA | 30 mg + 60 mg | 5 mg | 70 | 750 | 40 | 130 | 3 | 55 |

Figure 2:
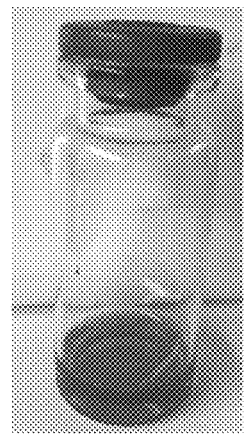
FIG. 2 shows a photograph of the dual-drug co-delivery system of the present invention.

Example 2: Loading Doxorubicin (1) 50.0-200.0 mg of block polymer was dissolved in 3 mL of phosphate buffer, stirred until completely dissolved, and obtained a clear solution D;
(2) Doxorubicin hydrochloride was dissolved in water and prepared an aqueous solution of Doxorubicin hydrochloride with a concentration of 3-8 mg/mL;
(3) The clear solution D and the micelle C loaded with Homoharringtonine obtained in Example 1 were mixed, and the obtained mixture was added 1 mL of the aqueous solution of Doxorubicin hydrochloride obtained in step (2) dropwise under heating at 25-70° C. and stirring at 100-1000 r/min for 20-120 min to obtain a solution E; the polymer of micelle C loaded with Homoharringtonine was the same as the polymer used in step (1);
(4) The solution E was allowed to stand at room temperature and filtered with a 0.22 μm polyethersulfone water-based filter membrane to remove the free drug that was not encapsulated into the micelle to obtain micelle F that simultaneously contained Homoharringtonine and Doxorubicin, i.e., the dual-drug co-delivery system of the present invention, as shown in FIG. 2, which was a clear red solution.

According to the above method, a series of dual-drug co-delivery systems were prepared. Only the parameters of loading Doxorubicin were adjusted. See Table 2 for details. By changing the volume of micelle C loaded with Homoharringtonine into the clear solution D, a dual-drug co-delivery system with different ratios of DOX and HHT could be obtained. The average hydration diameter was shown in Table 3.

TABLE 2

Parameters for loading Doxorubicin

| Example | Micelle C Category | Micelle C Volume/mL | Clear solution D Block copolymer | Concentration of Doxorubicin hydrochloride aqueous solution | Heating temperature | Stirring Rotate speed/r/min | Stirring Time/min | Encapsulation efficiency/ % |
|---|---|---|---|---|---|---|---|---|
| 1 | C-1 | 0.600 | Soluplus 95 mg | 5 mg/mL | 50° C. | 500 | 60 | 75 |
| 2 | C-2 | 0.800 | mPEG$_{2000}$-PCL$_{20000}$ 100 mg | 3 mg/mL | 70° C. | 100 | 100 | 70 |
| 3 | C-3 | 1.000 | DSPE-PEG$_{2000}$ 80 mg | 7 mg/mL | 25° C. | 1000 | 40 | 72 |
| 4 | C-4 | 1.200 | PLGA 150 mg | 6 mg/mL | 60° C. | 800 | 20 | 56 |
| 5 | C-5 | 1.500 | Polyoxyethylene polyoxypropylene ether block copolymer 100 mg | 8 mg/mL | 40° C. | 750 | 80 | 60 |
| 6 | C-6 | 1.200 | mPEG$_{2000}$-PCL$_{20000}$ + PLGA 100 mg | 6 mg/mL | 30° C. | 300 | 120 | 45 |
| 7 | C-1 | 0.320 | Soluplus 95 mg | 5 mg/mL | 50° C. | 500 | 60 | 75 |
| 8 | C-1 | 0.530 | Soluplus 95 mg | 5 mg/mL | 50° C. | 500 | 60 | 75 |

The average hydration diameter of micelle F in Example 2 was 80 nm (as shown in FIG. 1), the drug loading of Doxorubicin was 5%, and the encapsulation efficiency was 75%; the performance parameters of other examples were shown in Table 2 and Table 3.

TABLE 3

Dual-drug co-delivery system with different ratios of DOX and HHT

| Example | Average hydration diameter (nm) | Polydispersity index PDI | The mass ratio of DOX and HHT | Doxorubicin content/% | Homoharringtonin content/% |
| --- | --- | --- | --- | --- | --- |
| 1 | 80.0 ± 2.0 | 0.10 ± 0.01 | 8:1 | 5.5 | 0.7 |
| 2 | 91.4 ± 6.5 | 0.18 ± 0.01 | 4:1 | 2.0 | 0.5 |
| 3 | 78.1 ± 3.6 | 0.29 ± 0.05 | 7:1 | 5.1 | 0.7 |
| 4 | 160.4 ± 4.8 | 0.26 ± 0.06 | 4:1 | 2.0 | 0.5 |
| 5 | 130.1 ± 0.6 | 0.25 ± 0.03 | 6:1 | 3.6 | 0.6 |
| 6 | 140.7 ± 2.6 | 0.27 ± 0.08 | 3:1 | 2.1 | 0.7 |
| 7 | 85.2 ± 0.8 | 0.15 ± 0.04 | 15:1 | 5.8 | 0.4 |
| 8 | 82.5 ± 0.7 | 0.13 ± 0.04 | 9:1 | 4.6 | 0.5 |

Figure 3:
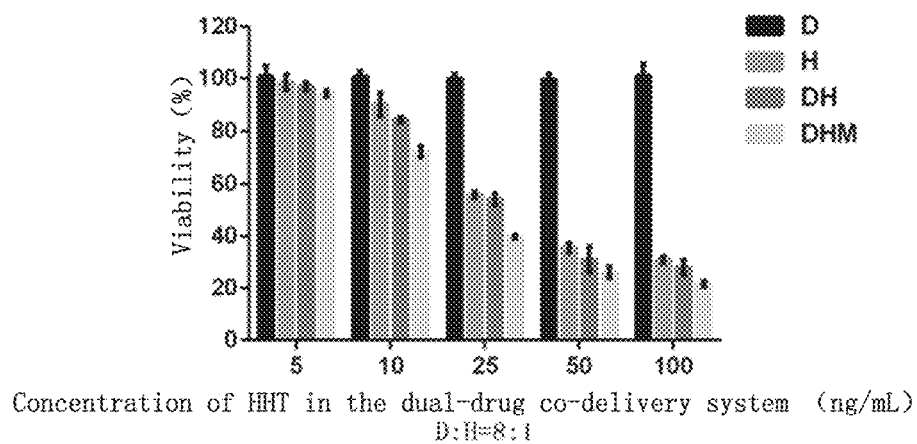
FIG. 3 is a bar graph showing the influence of the dual-drug co-delivery system of the present invention (the weight ratio of DOX and HHT is 8:1) on the viability of HL60/A cells.
Figure 4:
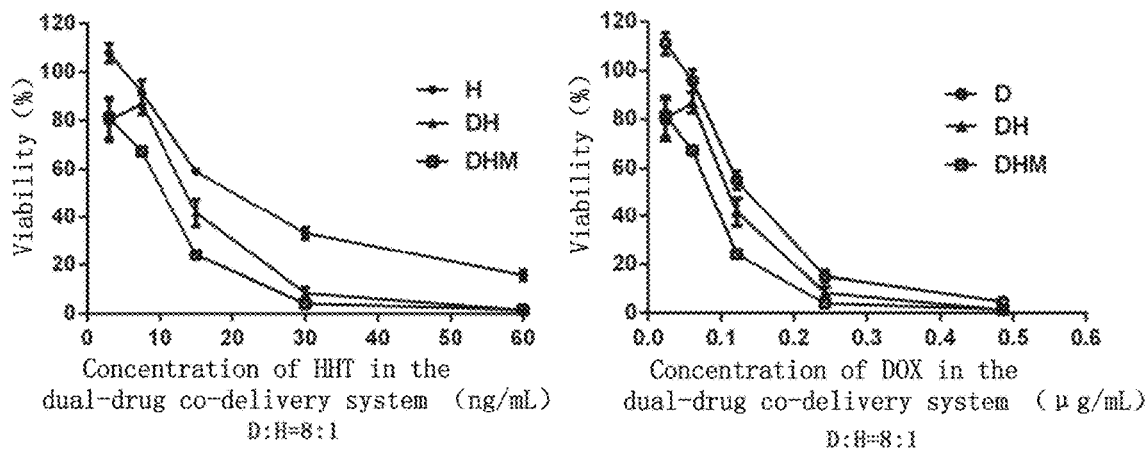
FIG. 4 is a graph showing the influence of the dual-drug co-delivery system of the present invention (the weight ratio of DOX and HHT is 8:1) on the viability of U937R cells.
Figure 5:
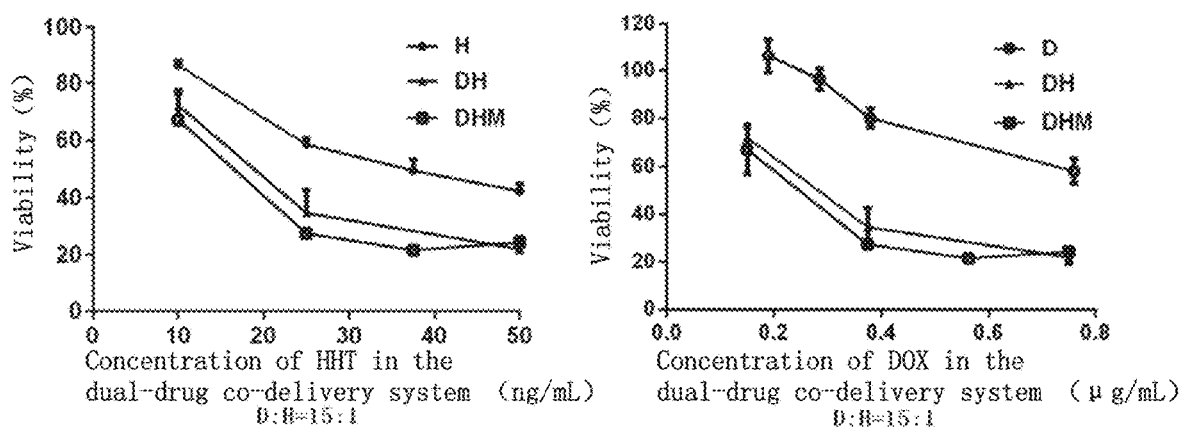
FIG. 5 is a graph showing the influence of the dual-drug co-delivery system of the present invention (the weight ratio of DOX and HHT is 15:1) on the viability of K562 cells.
Figure 6:
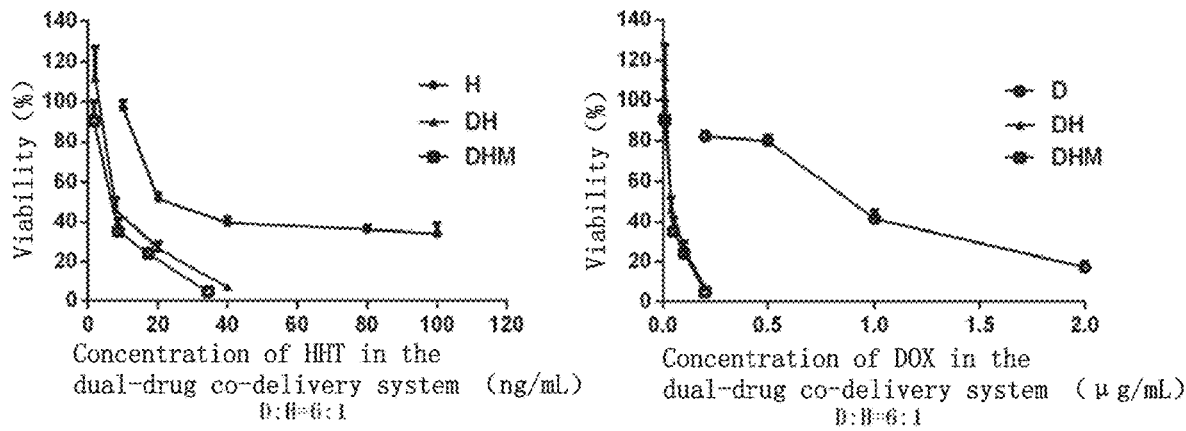
FIG. 6 is a graph showing the influence of the dual-drug co-delivery system of the present invention (the weight ratio of DOX and HHT is 6:1) on the viability of HeLa cells.
Figure 7:
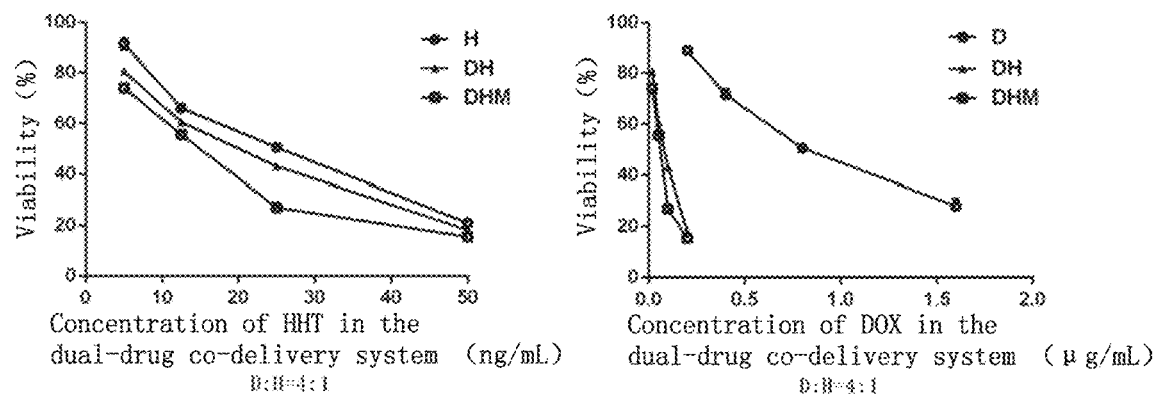
FIG. 7 is a graph showing the influence of the dual-drug co-delivery system of the present invention (the weight ratio of DOX and HHT is 4:1) on the viability of MCF7 cells.

Experiment 1: Inhibition of a Single Free Drug, Combination of Two Free Drugs and Dual-Drug Co-Delivery System on the Proliferation of Various Hematologic Tumors and Solid Tumor Cells In Vitro Taking HL60/A cells (HL60 cells resistant to Doxorubicin) as an example, the specific method was as follows:

The cells of $5 \times 10^4$ were seeded in each well in Corning 96-well U-shaped plate with 100 μL RPMI-1640 medium (containing 10% fetal bovine serum and 1% penicillin-streptomycin). Experimental groups include: 1) single HHT group (H): HHT was dissolved in dimethyl sulfoxide (DMSO) to obtain 10 mg/mL stock solution; 2) single DOX group (D): Doxorubicin hydrochloride was dissolved in water to obtain 5 mg/mL stock solution; 3) free drug combination group (DH): which was obtained by diluting stock solution 1) and 2) with culture medium respectively and mixed; the mass ratio of DOX to HHT was 8:1; (4) dual-drug co-delivery system group (DHM) of the present invention: which was obtained by diluting the dual-drug co-delivery systems of Examples 1-6 with culture medium, respectively. Each well of the control group was added with 100 μL of medium; 100 μL of diluted drug solution was added to each well in the experimental group to give final HHT concentrations of 5 ng/mL, 10 ng/mL, 25 ng/mL, 50 ng/mL and 100 ng/mL; the corresponding final concentrations of DOX were 40 ng/mL, 80 ng/mL, 200 ng/mL, 400 ng/mL, and 800 ng/mL. Cells in the Corning 96-well U plates were incubated for 24 h and then washed with PBS, 110 μL CCK8 dilution was added to each well and incubated for 2 h, and the absorbance values (OD) at wavelengths of 450 and 630 nm were measured using the microplate reader. The cell viability was calculated according to Formula 1. The results of Example 1 were shown in FIG. 3 as an example.

cell viability=$OD_{450\text{-}630}$(experimental group)/$OD_{450\text{-}630}$(control group)×100%　　Formula 1:

The results in FIG. 3 showed that when the HHT concentration was 25 ng/mL and DOX concentration was 200 ng/mL in the dual-drug co-delivery system, there was no cytotoxicity of single DOX against Doxorubicin-resistant strain HL60/A, and the cell viability was 56% under the action of single HHT, 54% under the action of free drug combination, and 40% under the action of dual-drug co-delivery system. Therefore, at the same drug concentration, the dual-drug co-delivery system of the present invention could inhibit the proliferation of tumor cells more effectively than single drug and free drug combination.

The dual-drug co-delivery system of the present invention also had similar effects on U937R (cytarabine-resistant strain, a drug-resistant cell line of acute myeloid leukemia screened by the inventor's laboratory), K562, HeLa and MCF7 cells. The culture conditions of each cell were shown in Table 4, and the results were shown in FIGS. 4-7.

For U937R cells, when the concentration of HHT in the dual-drug co-delivery system was 15 ng/mL and the concentration of DOX was 120 ng/mL, the cell viabilities under the action of single DOX, single HHT, free drug combination, and dual-drug co-delivery system of Example 1 of the present invention were 55%, 59%, 34%, and 21%, respectively.

For K562 cells, when the concentration of HHT in the dual-drug co-delivery system was 25 ng/mL and the concentration of DOX was 375 ng/mL, the cell viabilities under the action of single DOX, single HHT, free drug combination, and dual-drug co-delivery system of Example 7 of the present invention were 80%, 59%, 35%, and 27%, respectively.

For HeLa cells, when the concentration of HHT in the dual-drug co-delivery system was 20 ng/mL and the concentration of DOX was 120 ng/mL, the cell viabilities under the action of single DOX, single HHT, free drugs combination, and dual-drug co-delivery system of Example 5 of the present invention were 90%, 41%, 35%, and 30%, respectively.

For MCF7 cells, when the concentration of HHT in the dual-drug co-delivery system was 25 ng/mL and the concentration of DOX was 100 ng/mL, the cell viabilities under the action of single DOX, single HHT, free drug combination, and dual-drug co-delivery system in Example 4 of the present invention were 92%, 50%, 43%, and 27%, respectively.

TABLE 4

Culture conditions of tumor cells

| Tumor | Cell | Medium | Cell density | Weight ratio of DOX and HHT |
| --- | --- | --- | --- | --- |
| Hematologic tumor | HL60/A | RPMI-1640 | $5 \times 10^4$ cells/well | 8 |
|  | U937R |  |  | 8 |
|  | K562 |  |  | 15 |
| Solid tumor | HeLa | DMEM/high glucose | $1 \times 10^4$ cells/well | 6 |
|  | MCF7 |  |  | 4 |

Experiment 2: Influence of Free Drugs Combination and Dual-Drug Co-Delivery System on the Survival of AML1-ETO Mice The mice used in this experiment were 6-8 week old female C57 mice (from the Animal Experiment Center of the Institute of Basic Medical Sciences, Chinese Academy of Medical Sciences) were housed in an SPF class environment. Primary AML1-ETO mouse spleen cells (GFP-labeled) of $1 \times 10^6$ were suspended with 200 μL of ethylenediaminetetraacetic acid sodium salt (EDTA)/PBS and injected into sublethally irradiated (450 cGy) C57 mice via tail vein. Blood was collected from the tail vein of mice on the 7th day of transplantation, and the positive rate of peripheral blood leukemia cells was detected by flow cytometry to confirm the onset of disease in mice. The treatments were started from the $8^{th}$ day after transplantation, the following groups of drugs were injected intraperitoneally: (1) free drugs Homoharringtonine 0.4 mg/kg and Doxorubicin hydrochloride 3.6 mg/kg, as the DH group; (2) the dual-drug co-delivery system of Example 8 of the present invention (the mass ratio of DOX to HHT was 9:1), as the DHM group; (3) sterile PBS as a solvent control group (con group); (4) Soluplus 72 mg/kg dissolved in sterile PBS was used as the Soluplus group. The drug was administered for four consecutive days and then stopped for seven days, which constituted a course of treatment. The results were shown in FIG. 8.

Figure 8:
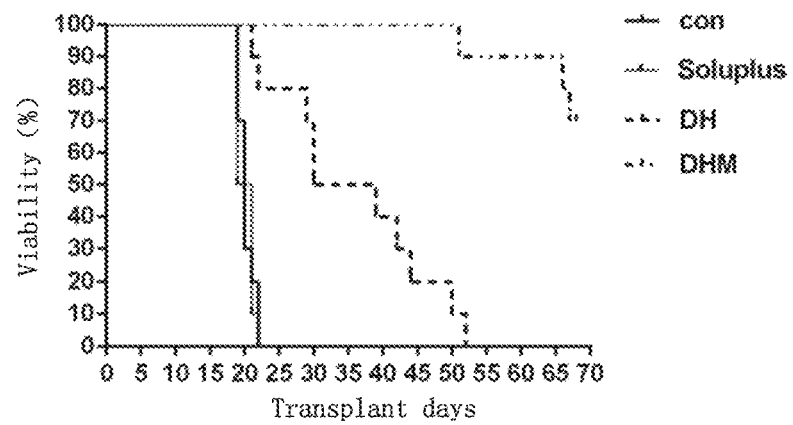
FIG. 8 is a graph showing that the dual-drug co-delivery system of the present invention (the weight ratio of DOX and HHT is 9:1) prolongs the survival period of leukemia mice.

The results in FIG. 8 showed that the terminal survival period of mice in the free drug combination group was 52 days; the survival rate of mice in the dual-drug co-delivery system group of the present invention was as high as 9/10 on the $52^{nd}$ day; the survival period of mice in the dual-drug co-delivery system group of the present invention was longer than that of the free drug combination group, and the difference was significant.

Figure 9:
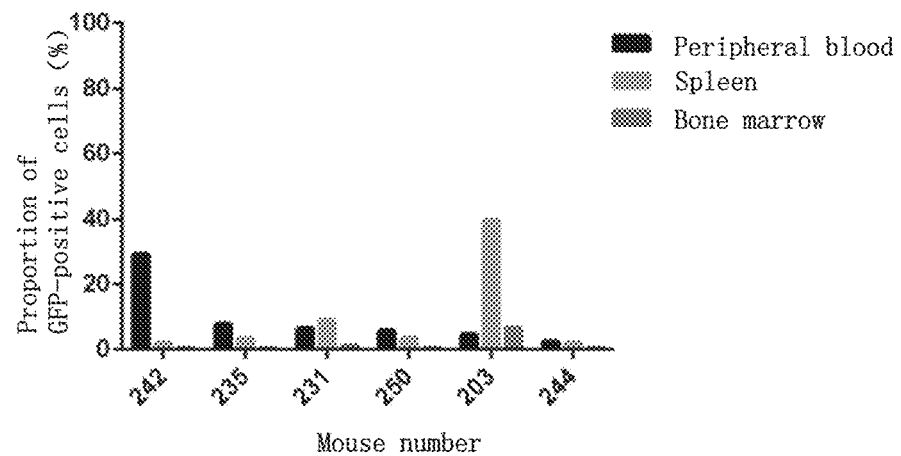
FIG. 9 is a bar graph showing that the dual-drug co-delivery system of the present invention (the weight ratio of DOX and HHT is 9:1) reduces the proportion of leukemia cells in mice.

On the $67^{th}$ day, the proportions of GFP-positive cells in peripheral blood (PB), spleen and bone marrow of the surviving mice in the DHM group were detected. FIG. 9 showed the results of leukemia cell infiltration in different organs of each mouse. The results in FIG. 9 showed that the dual-drug co-delivery system of the present invention could prolong the survival period of mice and at the same time reduce the infiltration of leukemia cells in various organs.

Experiment 3: The Efficacy of Free Drug Combination and Dual-Drug Co-Delivery System on AML1-ETO Mice The experiment process was the same as Experiment 2.

Mice were executed after one treatment course, and the proportions of GFP-positive cells in peripheral blood (PB) and bone marrow (Bone) were detected by flow cytometry. Meanwhile, the numbers of white blood cells (WBC), red blood cells (RBC) and platelets (PLT) in the peripheral blood were detected using a blood cell analyzer (Myriad BC-5120 model). The results were shown in FIG. 10 and FIG. 11.

Figure 10:
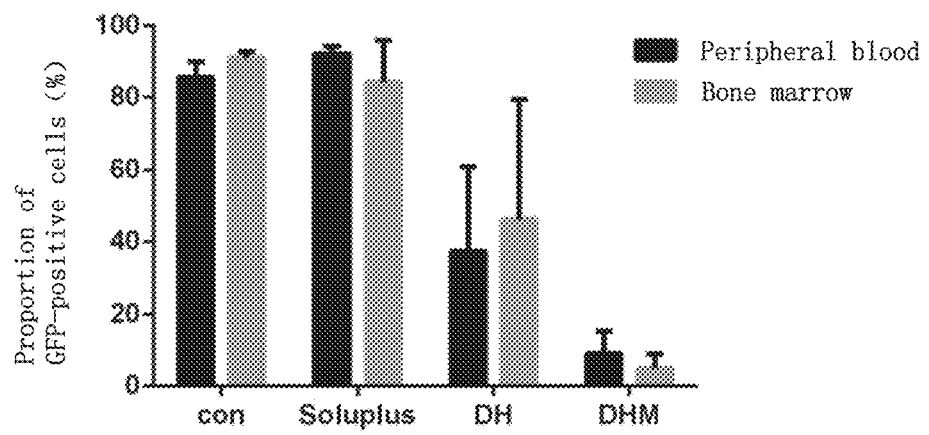
FIGS. 10-11 are bar graphs showing that the dual-drug co-delivery system of the present invention (the weight ratio of DOX and HHT is 9:1) reduces toxic side effects.
Figure 11:
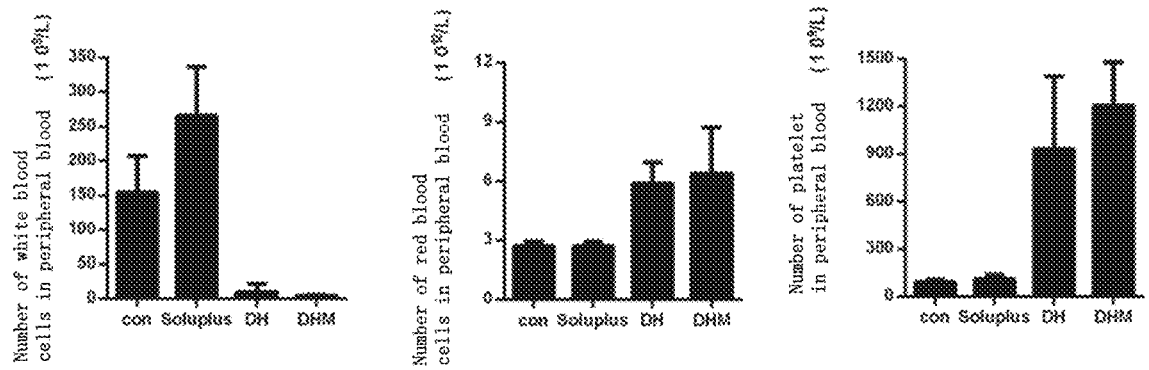

The result of FIG. 10 showed that the proportion of leukemia cells in the peripheral blood of the DHM group decreased from 40% of the DH group to 10% after treatment; the proportion of leukemia cells in the bone marrow decreased from 50% of the DH group to 5%, indicating that DHM could significantly reduce the proportions of leukemia cells in the peripheral blood and bone marrow. The result of FIG. 11 showed that after treatment, WBC in DHM group decreased from $10 \times 10^9$/L in DH group to $5 \times 10^9$/L, RBC increased from $5.9 \times 10^{12}$/L in DH group to $6.4 \times 10^{12}$/L, and PLT increased from $9.3 \times 10^{11}$/L in DH group to $1.2 \times 10^{12}$/L; indicating that DHM treatment did not reduce the numbers of red blood cells and platelets while reducing leukemia cells, indicating that it had no inhibitory effect on bone marrow cells and could reduce toxic side effects while exerting a therapeutic effect.

INDUSTRIAL APPLICABILITY

The dual-drug co-delivery system provided by the present invention has a killing effect on a variety of hematologic tumors and solid tumor cells, while reducing toxic side effects, and can inhibit tumor growth and can be used for leukemia treatment; the preparation process does not use any organic solvent, the preparation process is simple and suitable for industrial applications.

The invention claimed is:

1. A dual-drug co-delivery system prepared from raw materials including a block copolymer, Homoharringtonine and Doxorubicin hydrochloride, wherein the block copolymer is selected from one or more of polyethylene capro-lactam-polyvinyl acetate-polyethylene glycol (Soluplus), methoxy polyethylene glycol-polycaprolactone (mPEG-PCL), distearoyl phosphatidylethanolamine-polyethylene glycol 2000 ($DSPE-PEG_{2000}$), polyoxyethylene polyoxy-propylene ether block copolymer, polylactic acid-hydroxy-acetic acid copolymer (PLGA), wherein in the dual-drug co-delivery system, the block copolymer serves as a carrier and forms a micelle with a hydrophilic shell-hydrophobic core structure, and the Homoharringtonine and Doxorubicin hydrochloride are encapsulated in the hydrophobic core of the micelle.

2. The dual-drug co-delivery system according to claim 1, wherein the ratio of Homoharringtonine, Doxorubicin hydrochloride, and the block copolymer in parts by weight is (1-10):(1-40):(4-200).

3. The dual-drug co-delivery system according to claim 1, wherein the average hydration diameter of the dual-drug co-delivery system is 20-200 nm.

4. The dual-drug co-delivery system according to claim 1, wherein the block copolymer is Soluplus, and the molecular weight ratio of polyethylene caprolactam, polyvinyl acetate and polyethylene glycol in the block copolymer Soluplus is 57:30:13.

5. The dual-drug co-delivery system according to claim 4, wherein the ratio of Homoharringtonine, Doxorubicin hydrochloride, and the block copolymer Soluplus in parts by weight is (1-10):(1-40):(4-200).

6. A method for preparing the dual-drug co-delivery system of claim 1, comprises the following steps of:
   1) preparing a micelle C by:
      adding the block copolymer and Homoharringtonine to a phosphate buffer, heating and stirring to obtain a liquid B, and
      filtering the liquid B and collecting the filtrate, which is the micelle C;
   2) preparing a clear solution D by:
      dissolving the block copolymer in a phosphate buffer;
   3) mixing the micelle C with the clear solution D to obtain a mixture; and
   4) adding an aqueous solution of Doxorubicin hydrochloride to the mixture to obtain the dual-drug co-delivery system.

7. The method according to claim 6, wherein the step of adding an aqueous solution of Doxorubicin hydrochloride to the mixture is performed by adding dropwise under heating and stirring.

8. The method according to claim 7, wherein the heating is heated to 25-70° C.

9. The method according to claim 7, wherein the stirring speed is 100-1000 r/min.

10. The dual-drug co-delivery system according to claim 2, wherein the ratio of Homoharringtonine, Doxorubicin hydrochloride, and the block copolymer in parts by weight is (1-5):(3-15):(45-200).

11. The dual-drug co-delivery system according to claim 3, wherein the average hydration diameter of the dual-drug co-delivery system is 60-180 nm.

12. The dual-drug co-delivery system according to claim 5, wherein the ratio of Homoharringtonine, Doxorubicin hydrochloride, and the block copolymer Soluplus in parts by weight is (1-5):(3-15):(45-200).

13. The method according to claim 6, wherein the concentration of Doxorubicin hydrochloride in the aqueous solution of Doxorubicin hydrochloride is 3-8 mg/mL.

14. The dual-drug co-delivery system according to claim 1, wherein the dual-drug co-delivery system is prepared through the following steps of:

1) preparing a micelle C by:
    adding the block copolymer and Homoharringtonine to a phosphate buffer, heating and stirring to obtain a liquid B, and
    filtering the liquid B and collecting the filtrate, which is the micelle C;
2) preparing a clear solution D by:
    dissolving the block copolymer in a phosphate buffer;
3) mixing the micelle C with the clear solution D to obtain a mixture; and
4) adding an aqueous solution of Doxorubicin hydrochloride to the mixture to obtain the dual-drug co-delivery system.

15. The dual-drug co-delivery system according to claim 14, wherein the step 4) is performed by adding dropwise under heating and stirring.

16. The dual-drug co-delivery system according to claim 15, wherein the heating is heated to 25-70° C., and the stirring speed is 100-1000 r/min.

* * * * *